(12) United States Patent
Mazgalev et al.

(10) Patent No.: US 7,860,566 B2
(45) Date of Patent: Dec. 28, 2010

(54) SYSTEM AND METHOD FOR ACHIEVING REGULAR SLOW VENTRICULAR RHYTHM IN RESPONSE TO ATRIAL FIBRILLATION

(75) Inventors: Todor N. Mazgalev, Pepper Pike, OH (US); Youhua Zhang, Cleveland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 686 days.

(21) Appl. No.: 11/244,896

(22) Filed: Oct. 6, 2005

(65) Prior Publication Data
US 2007/0083242 A1 Apr. 12, 2007

(51) Int. Cl.
*A61N 1/362* (2006.01)
(52) U.S. Cl. ............................. 607/14; 607/4
(58) Field of Classification Search ............... 607/14, 607/2, 9
See application file for complete search history.

(56) References Cited

U.S. PATENT DOCUMENTS

| | | | |
|---|---|---|---|
| 4,363,325 A * | 12/1982 | Roline et al. | 607/9 |
| 4,979,511 A | 12/1990 | Terry, Jr. | |
| 5,154,172 A | 10/1992 | Terry, Jr. et al. | |
| 5,179,950 A | 1/1993 | Stanislaw | |
| 5,186,170 A | 2/1993 | Varrichio et al. | |
| 5,188,104 A | 2/1993 | Wernicke et al. | |
| 5,203,326 A | 4/1993 | Collins | |
| 5,215,086 A | 6/1993 | Terry, Jr. et al. | |
| 5,231,988 A | 8/1993 | Wernicke et al. | |
| 5,235,980 A | 8/1993 | Varrichio et al. | |
| 5,237,991 A | 8/1993 | Baker, Jr. et al. | |
| 5,251,634 A | 10/1993 | Weinberg | |
| 5,263,480 A | 11/1993 | Wernicke et al. | |
| 5,269,303 A | 12/1993 | Wernicke et al. | |
| 5,299,569 A | 4/1994 | Wernicke et al. | |
| 5,330,507 A | 7/1994 | Schwartz | |
| 5,330,515 A | 7/1994 | Rutecki et al. | |
| 5,334,221 A | 8/1994 | Bardy | |
| 5,335,657 A | 8/1994 | Terry, Jr. et al. | |

(Continued)

OTHER PUBLICATIONS

Tosato et al., "Heart Rate Control Through Vagal Nerve Stimulation", *9th Annual Conference of the International FES Society*, Sep. 2004.

*Primary Examiner*—Carl H Layno
*Assistant Examiner*—Brian T Gedeon
(74) *Attorney, Agent, or Firm*—Tarolli, Sundheim, Covell & Tummino LLP (57) ABSTRACT

A system (10) for achieving a desired cardiac rate and cardiac rhythm in response to atrial fibrillation in a heart includes an atrial fibrillation (AF) detector (40) for detecting AF. The system also includes an atrioventricular node vagal stimulator (AVN-VS) (30) for stimulating vagal nerves associated with an atrioventricular (AV) node of the heart. The system further includes an on-demand pace maker (40) for providing ventricular pacing stimulation to the heart. A control unit (20) is operatively connected with the AF detection device, the AVN-VS device, and the on-demand pacing device. The control unit is responsive to AF detection by the AF detector to cause the AVN-VS to stimulate the vagal nerves to help reduce the ventricular rate of the heart. The control unit is further responsive to AF detection by the AF detector to cause the on-demand pace maker to help regulate the ventricular rate of the heart.

19 Claims, 6 Drawing Sheets

U.S. PATENT DOCUMENTS

| | | | | |
|---|---|---|---|---|
| 5,351,394 | A | 10/1994 | Weinberg | |
| 5,356,425 | A | 10/1994 | Bardy et al. | |
| 5,411,531 | A | 5/1995 | Hill et al. | |
| 5,531,778 | A | 7/1996 | Maschino et al. | |
| 5,540,730 | A | 7/1996 | Terry, Jr. et al. | |
| 5,571,150 | A | 11/1996 | Wernicke et al. | |
| 5,690,681 | A | 11/1997 | Geddes et al. | |
| 5,707,400 | A | 1/1998 | Terry, Jr. et al. | |
| 5,916,239 | A | 6/1999 | Geddes et al. | |
| 5,928,272 | A | 7/1999 | Adkins et al. | |
| 6,006,134 | A | 12/1999 | Hill et al. | |
| 6,240,314 | B1 * | 5/2001 | Plicchi et al. | 607/14 |
| 6,434,424 | B1 * | 8/2002 | Igel et al. | 607/9 |
| 6,473,644 | B1 | 10/2002 | Terry, Jr. et al. | |
| 6,510,342 | B1 | 1/2003 | Park et al. | |
| 6,519,493 | B1 | 2/2003 | Florio et al. | |
| 6,587,719 | B1 | 7/2003 | Barrett et al. | |
| 6,600,956 | B2 | 7/2003 | Maschino et al. | |
| 6,606,517 | B1 | 8/2003 | Park et al. | |
| 6,609,025 | B2 | 8/2003 | Barrett et al. | |
| 6,622,038 | B2 | 9/2003 | Barrett et al. | |
| 6,622,041 | B2 | 9/2003 | Terry, Jr. et al. | |
| 6,622,047 | B2 | 9/2003 | Barrett et al. | |
| 6,721,603 | B2 | 4/2004 | Zabara et al. | |
| 6,804,556 | B1 | 10/2004 | Florio et al. | |
| 6,934,583 | B2 * | 8/2005 | Weinberg et al. | 607/9 |
| 2005/0010263 | A1 | 1/2005 | Schauerte | |
| 2005/0197675 | A1 * | 9/2005 | David et al. | 607/9 |

* cited by examiner

SYSTEM AND METHOD FOR ACHIEVING REGULAR SLOW VENTRICULAR RHYTHM IN RESPONSE TO ATRIAL FIBRILLATION

TECHNICAL FIELD

The present invention relates to a system and method for treating cardiac arrhythmia. More particularly, the present invention relates to a system and method for achieving regular slow ventricular rhythm in response to atrial fibrillation.

BACKGROUND OF THE INVENTION

Cardiac arrhythmia are common and potentially dangerous medical aliments associated with abnormal cardiac chamber wall tissue. Characteristic of cardiac arrhythmia, abnormal regions of cardiac tissue do not follow the synchronous beating cycle associated with normal cardiac tissue. The abnormal cardiac tissue regions conduct electrical activity to adjacent tissue with aberrations that disrupt the cardiac cycle, creating an asynchronous cardiac rhythm. Various serious conditions, such as stroke, heart failure, and other thromboembolic events, can occur as a result of cardiac arrhythmia.

One particular type of cardiac arrhythmia is atrial fibrillation (AF). Atrial fibrillation is recognized as the most common clinically significant cardiac arrhythmia and increases significantly the morbidity and mortality of patients. Current data estimates that 2.3 million Americans experience AF. Since the prevalence of AF increases with age, and due to the aging population, the number of AF patients is estimated to increase 2.5 times during the next 50 years.

Atrial fibrillation usually results in a rapid ventricular rate and an irregular ventricular rhythm that produce undesirable negative hemodynamic effects. Long-term uncontrolled rapid ventricular rate could, for example, lead to tachycardia-induced cardiomyopathy. Irregular ventricular rhythm may independently produce detrimental consequences and may cause symptoms in some patients, even when the ventricular rate is controlled. It is therefore desirable to achieve ventricular rate control and ventricular rhythm regularization during AF.

A variety of medical procedures have been developed to help treat cardiac arrhythmia. Drug therapy is the most common approach to achieve slow ventricular rate in AF patients. Drug therapy may, however, may be ineffective or not well tolerated. Partial ablative procedures, such as AV node modification, have been shown to be effective in reducing ventricular rate in some drug-refractory AF patients. However, due to the risk of AV block associated with AV node modification, this therapy is recommended only when AV nodal ablation with pacemaker implantation is intended. Although AV nodal ablation with right ventricular pacing has been shown to be beneficial in improving symptoms, quality of life, and exercise duration in drug-refractory patients with AF, it creates permanent AV block and results in lifelong pacemaker dependency.

SUMMARY OF THE INVENTION

The present invention relates to a system and method for treating cardiac arrhythmia. More specifically, the present invention relates to a system and method for achieving regular slow ventricular rhythm in response to atrial fibrillation. In one particular aspect, the system and method involves the use of AV node selective vagal stimulation and ventricular on-demand pacing to achieve regular slow ventricular in response to atrial fibrillation.

The present invention also relates to a system for achieving a desired cardiac rate and cardiac rhythm in response to atrial fibrillation in a heart. The system includes atrial fibrillation (AF) detecting means for detecting AF. The system also includes atrioventricular node vagal stimulation (AVN-VS) means for stimulating vagal nerves associated with a atrioventricular (AV) node of the heart. The system also includes on-demand pacing means for providing ventricular pacing stimulation to the heart. The system further includes control means operatively connected with the AF detecting means, the AVN-VS means, and the on-demand pacing means. The control means is responsive to AF detection by the AF detecting means to cause the AVN-VS means to stimulate the vagal nerves to help reduce the ventricular rate of the heart. The control means is further responsive to AF detection by the AF detecting means to cause the on-demand pacing means to help regulate the ventricular rate of the heart.

The present invention also relates to a system for achieving a desired cardiac rate and cardiac rhythm in response to atrial fibrillation in a heart. The system includes an atrial fibrillation (AF) detector for detecting atrial fibrillation in the heart. The system also includes an atrioventricular node vagal stimulation (AVN-VS) electrode for stimulating vagal nerves associated with an atrioventricular (AV) node of the heart. The system also includes an on-demand pacing electrode for providing ventricular pacing stimulation to the heart. The system also includes a control unit operatively connected with the AF detector, the AVN-VS electrode, and the on-demand pacing electrode. The control unit is operative to determine an AF episode via the AF detector. The control unit is also operative to provide an electrical signal to the AVN-VS electrode to stimulate the vagal nerves to help reduce the ventricular rate of the heart in response to determining an AF episode. The control means is further operative to provide an electrical signal to the on-demand pacing electrode to stimulate the heart to help regulate the ventricular rate of the heart in response to determining an AF episode.

The present invention further relates to a method for achieving a desired cardiac rate and cardiac rhythm in response to atrial fibrillation in a heart. The method includes the steps of stimulating vagal nerves associated with an atrioventricular (AV) node of the heart to reduce the cardiac rate and applying ventricular pacing stimulation to regulate the ventricular rhythm of the heart.

DESCRIPTION OF THE DRAWINGS

The foregoing and other features of the present invention will become apparent to those skilled in the art to which the present invention relates upon reading the following description with reference to the accompanying drawings, in which.

DESCRIPTION OF EMBODIMENTS

Figure 1:
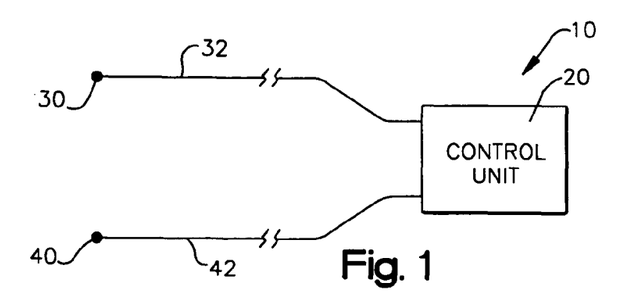
FIG. 1 is a schematic illustration of a system for treating cardiac arrhythmia in accordance with a first example embodiment of the present invention.

The present invention relates to a system and method for treating cardiac arrhythmia and, in particular, a system and method for treating atrial fibrillation (AF). Representative of the present invention, FIG. 1 illustrates an example configuration of a system 10 for combining AV node vagal stimulation (AVN-VS) with on-demand pacing, such as VVI pacing, to achieve a desired ventricular rate with a desired ventricular rhythm in response to atrial fibrillation. For example, the system 10 may combine AVN-VS and on-demand pacing to achieve a relatively slow ventricular rate with a substantially regular ventricular rhythm. In the example embodiment of FIG. 1, the system 10 includes a control unit 20, one or more vagal stimulation (VS) electrodes 30, and one or more pacing electrodes 40. The VS electrodes 30 are operatively connected with the control unit 20 via VS leads 32. The pacing electrodes 40 are operatively connected with the control unit 20 via pacing leads 42.

The control unit 20 is operative to provide electrical stimulation signals to the VS electrodes 30 and the pacing electrodes 40 via the leads 32 and 42, respectively. The control unit 20 modulates or controls the frequency, amplitude, duration/pulse-width of the stimulation signals in accordance with the description set forth below in order to achieve the desired ventricular rate and rhythm. The control unit 20 may also be operative to monitor cardiac activity, such as R waves, via the pacing electrodes 40.

Figure 2:
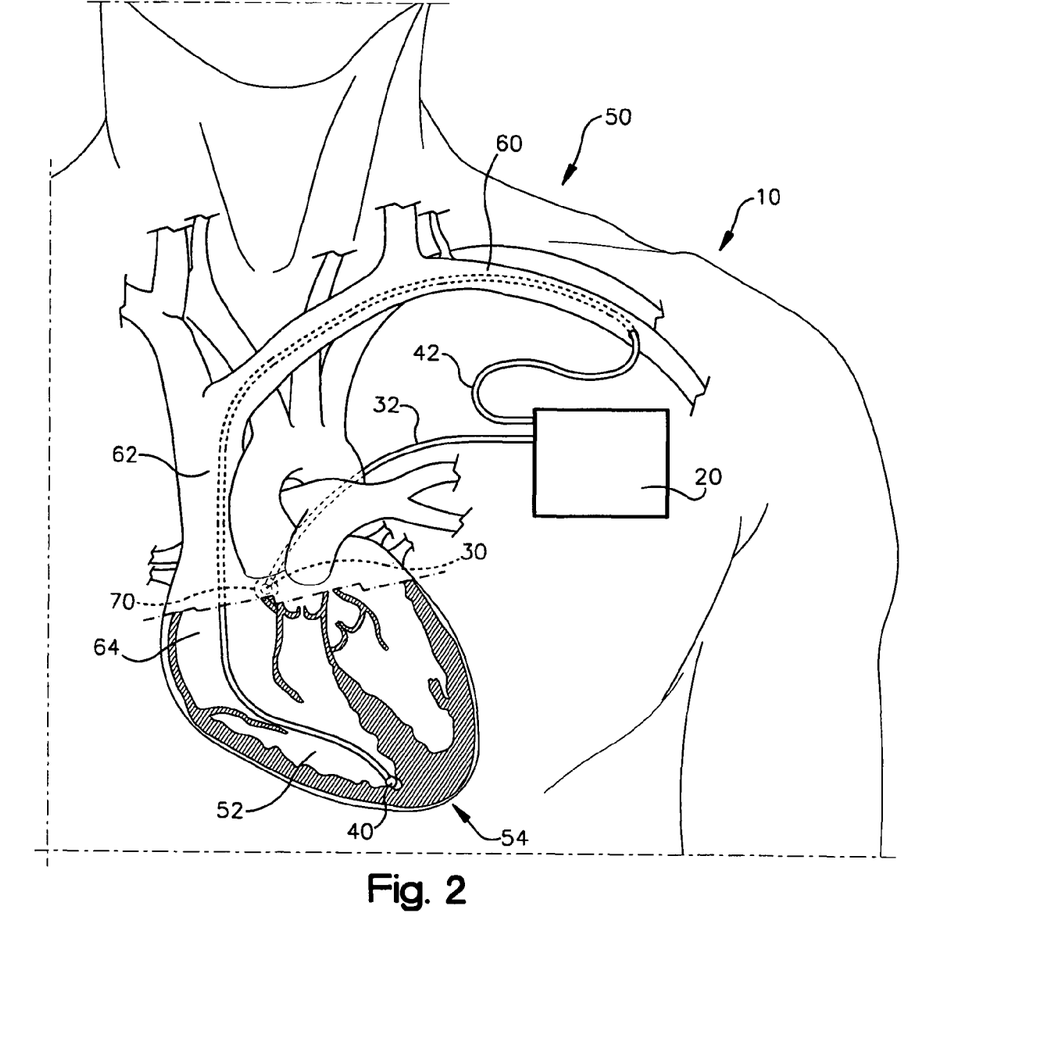
FIG. 2 illustrates a patient outfitted with the system of FIG. 1.

Referring to FIG. 2, a patient 50 is outfitted with the system 10 of the example embodiment of FIG. 1. The pacing electrodes 40 are delivered and implanted in the right ventricle 52 of the patient's heart 54 via blood vessels, which may be accessed by known means (not shown), such as by cannulization and catheterization of the vessels. In the embodiment of FIG. 2, the pacing electrodes 40 are inserted into the left brachiocephalic vein 60, pass through the superior vena cava 62 and right atrium 64, and are delivered to the right ventricle 52 (e.g., the right ventricular apex) of the patient's heart 54. While this procedure is commonly used to deliver the pacing electrodes 40, those skilled in the art will appreciate that the pacing electrodes may be delivered to the right ventricle 52 in any suitable alternative manner.

In the embodiment of FIG. 2, the VS electrodes 30 are implanted or otherwise positioned on an AV nodal fat pad 70 of the patient's heart 54. The AV nodal fat pad 70 is an epicardial fat pad located adjacent the posterior AV groove of the heart 54. The AV nodal fat pad 70 is rich with vagal nerves/nerve fibers. The VS electrodes 30 may be positioned on the AV nodal fat pad 70 in a variety of manners. For example, the VS electrodes 30 may be positioned on the AV nodal fat pad 70 via a surgical procedure in which the patient's chest cavity is opened and the electrodes are positioned on the heart 54 directly. Those skilled in the art will appreciate, however, that the VS electrodes 30 may be positioned on the AV nodal fat pad 70 in an alternative manner, such as via a minimally invasive surgical procedure.

The control unit 20 may be implanted subcutaneously in the chest area of the patient 50, as shown in FIG. 2. As known in the art, the pacing electrodes 30 may also serve as sensors for monitoring the electrical activity of the heart 54, such as the R-R intervals of the heart. The control unit 20 may thus monitor the rate or rhythm of the heart 54 via the pacing electrodes 30 and may detect the occurrence of atrial fibrillation. Alternatively, separate electrodes (not shown) may be used to detect AF. The system 10 thus may be an active or "on-demand" system in which ventricular rate and rhythm control is applied in response to detection to an AF episode.

Figure 3:
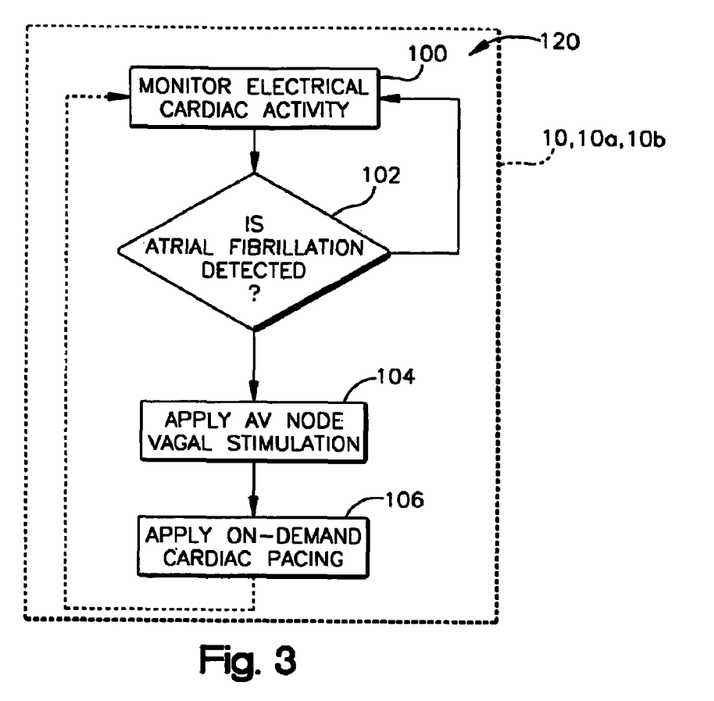
FIG. 3 is a schematic block diagram of a process performed by the system of FIG. 1.

FIG. 3 illustrates a functional block diagram depicting a process 120 performed by the system 10 of FIGS. 1 and 2 in accordance with the present invention. Referring to FIG. 3, at 100, the system 10 monitors electrical cardiac activity. At 102 a determination is made as to whether atrial fibrillation is detected. If atrial fibrillation is not detected, the system 10 reverts to 100 and continues to monitor the cardiac electrical activity. The system 10 thus may provide continuous monitoring of cardiac electrical activity for the occurrence of atrial fibrillation.

If, at 102, atrial fibrillation is detected, the system 10 proceeds to 104 and applies AVN-VS. In the embodiment illustrated in FIG. 2, the control unit 20 delivers electrical stimulation to the AV nodal fat pad 70 via the VS electrodes 30 and lead 32. This AVN-VS is effective to reduce the ventricular rate during AF. By titrating or modulating the energy delivered to the AV nodal fat pad 70, the average ventricular rate can be controlled (i.e., lowered) to or toward a desired value.

At 104, the control unit may implement an open loop control algorithm for applying the AVN-VS energy. In this example configuration, the AVN-VS energy may be applied at a constant predetermined level or intensity to lower the ventricular rate during AF. The rate to which the ventricular rate is lowered may depend on a variety of factors, such as the ventricular rate at the onset of AF and the particular physiological cardiac conditions of the particular patient. Thus, in an open loop control configuration, the ventricular rate is lowered using AVN-VS without being controlled to a particular desired rate.

Alternatively, at 104, the control unit 20 may implement a closed loop control algorithm to control the AVN-VS in order to achieve a particular desired ventricular rate. The closed loop algorithm implemented in the control unit 20 may be any algorithm suited to achieve active feedback control. For example, a classic proportional-integral-derivative (PID) control algorithm may be implemented in the control unit 20. In this example configuration, the control unit 20 would measure the instantaneous heart rate based on the time interval between two successive heart beats. This instantaneous heart rate would then be compared to the desired ventricular rate to determine an error value, which is provided to the PID control algorithm. Based on the error value, the PID control algorithm calculates an increase or decrease in the intensity of the AVN-VS energy to control or "steer" the ventricular rate toward the desired value. This control loop continues until a zero-error condition is achieved. Through implementation of the closed loop control algorithm, the control unit 20 may thus maintain the ventricular rate at the desired value.

According to the present invention, with the average ventricular rate is adjusted to the desired value using AVN-VS procedure described above, the system 10 proceeds to 106, where the ventricular rhythm is normalized via on-demand ventricular pacing (e.g., VVI pacing). Referring to FIG. 2, the control unit 20 delivers electrical stimulation to the cardiac tissue of the right ventricle 52 via the pacing electrodes 40 and lead 42. This on-demand pacing is effective to help normalize the ventricular rhythm brought about by the AF. By controlling the frequency, amplitude, or both the frequency and amplitude with which the energy is delivered to the right ventricle 52, the ventricular rhythm can be controlled to help maintain a desired ventricular rhythm. Thus, according to the present invention, the system 10 combines the AVN-VS and on-demand ventricular pacing to help achieve a regular slow ventricular rate in response to AF. The system 10 may achieve this purpose while avoiding the use of AVN ablation and medication therapy.

The description set forth above regarding the process 120 performed by the system 10 is not meant to limit the steps to any sequence or order. For example, while the steps of applying AVN-VS (step 104) and on-demand pacing (step 106) appear as being performed in a particular sequence, these steps could be performed in any order or simultaneously. In fact, the steps of monitoring cardiac activity 100, determining the occurrence of AF 102, applying AVN-VS 104, and applying on-demand pacing 106 may all be performed simultaneously.

On-demand ventricular (VVI) pacing, when initiated during AF, helps eliminate R-R intervals longer than the pacing interval. A progressively increasing pacing rate can also eliminate many of the R-R intervals that are shorter than the pacing interval. When the pacing rate is faster than the average intrinsic ventricular rate during AF, it has been found that a regular ventricular rhythm ensues. Thus, when the intrinsic ventricular rate is already excessively rapid during AF, the required pacing rate would be unacceptably high, rendering the on-demand pacing method impractical for clinical applications. The specific pacing rate required to achieve regularization is thus directly linked to the spontaneous ventricular rate during AF. Therefore, regularization at a desired rate level could be achieved if the average intrinsic ventricular rate during AF is slowed down first. According to the present invention, the application of AVN-VS prior to ventricular pacing helps lower the average ventricular rate to a level at which an increase induced by subsequent ventricular pacing remains at an acceptable level.

On-demand pacing as a rate regularization tool necessitates relatively short pacing intervals. For example, a significant reduction of irregularity during AF can be achieved at a cost of about 2% to 17% increase of ventricular rate. However, because the ventricular rate during AF frequently is quite rapid without medications, such an increase in the ventricular rate may be undesirable. On-demand pacing could thus be viewed as being somewhat limited due to concerns over elevating the ventricular rate to dangerously high levels.

Instead of using on-demand ventricular pacing as the ventricular rate slowing mechanism, the present invention utilizes neural control of AV transmission during AF (i.e., AVN-VS) to slow the ventricular rate. AVN-VS takes advantage of the rich and selective supply of vagal nerves to the AV node, which exert negative dromotropic effect. By modulating the stimulation amplitude applied during AVN-VS, one can achieve graded ventricular rate slowing in order to reach an optimal hemodynamic response.

This pacing strategy is mechanistically based on suppression of conduction through the AVN as a result of collision of anterograde and retrograde wavefronts. To begin with, AF itself has been shown to result in random, high-rate bombardment at the AVN inputs, resulting in subsequent concealed conduction of multiple impulses. While the precise mechanism of concealment remains undetermined, it certainly depends on the delayed recovery of nodal excitability as reflected in the "refractory" theory for ventricular response in AF. Whether or not associated with decremental conduction, the coexistence of multiple anterograde impulses should result in collision, intranodal block(s), and electrotonic events that modulate subsequent propagation. As postulated by the "interception" theory and demonstrated in modeling studies, in these conditions retrograde impulses invading the AVN are followed by refractoriness with slow recovery of excitability, setting the stage for electrotonic inhibition of anterograde impulses.

Therefore, it is most likely that ventricular pacing at a rate equal to or above that present during AF results in a critical degree of collision/annihilation of retrograde and anterograde impulses in the AVN. The major role of the AVN-VS would be to further inhibit the propagation through the AVN during AF. Because a reduced number of atrial impulses would successfully traverse the node, a comparatively lower rate VVI pacing would be necessary to counteract them and achieve the effect of "electrical jam." Thus, AVN-VS accentuates the VVI effect by permitting full elimination of anterograde propagation of fibrillatory impulses at substantially lower rates.

Experimental Data

To determine the efficacy of the systems and methods described herein, experiments were performed on adult canine specimens (body weight 21-30 kg). The specimens were anesthetized and ventilated with room air supplemented with oxygen as needed to maintain normal arterial blood gases. The left external jugular vein was cannulated, and normal saline was infused at 100 to 200 mL/h to replace spontaneous fluid losses. Standard surface ECG leads I, II, and III were monitored continuously throughout the entire study. Intermittent arterial blood gas measurements were taken, and adjustments of ventilator were made to correct metabolic abnormalities. Body temperature was monitored and maintained at 36 to 37° C. using an electrical heating pad placed under the specimen and operating room lamps.

Micromanometer-tipped catheters were inserted through cannulated femoral and carotid arteries and advanced to the thoracic aorta and left ventricle (LV), respectively, to record blood pressure and LV pressure. After the chest was opened through a median sternotomy, a cardiac output probe was placed around the aorta and connected to a flow meter to measure aortic flow. Custom-made quadripolar plate electrodes were sutured to the high right atrium and right ventricular apex for bipolar pacing and recording. Atrial pacing was used to induce AF, whereas ventricular VVI pacing was used for rate regularization. A bipolar stimulating electrode was sutured to the epicardial fat pad (the inferior vena cava-left atrium fat pad) that contains parasympathetic neural pathways selectively innervating the AVN. All signals (surface ECG, right atrial and right ventricular ECGs, aortic blood pressure, LV pressure, and aortic flow signals) were properly amplified, filtered, and for purposes of display and recording.

AVN-VS was delivered to the inferior vena cava-left atrium fat pad by a computer-controlled feedback program to achieve three levels (targets) of average ventricular rate slowing. These targets were defined as 75%, 100%, and 125% of the corresponding spontaneous sinus cycle length (SCL) present before AF was induced. The program implemented a classic, proportional-integral-derivative closed-loop process control in delivering the AVN-VS. To achieve target ventricular rate levels during AF, AVN-VS was delivered as short bursts synchronized with the right ventricular electrogram. After each target rate was achieved, VVI pacing was initiated at a rate equal to the achieved target while maintaining delivery of the AVN-VS.

After surgical preparation and at least 30 minutes of stabilization, SCL was determined. AF then was induced and maintained by rapid right atrial pacing (20 Hz, 2 ms). After at least 15 minutes of stabilization, the ventricular rate was determined on-line by averaging 500 cardiac cycles collected during AF. Then, while maintaining AF, the feedback computer program was initiated to deliver the AVN-VS and to slow the average ventricular rate to 1 of 3 target levels: 75%, 100%, or 125% of the corresponding SCL. The computerized AVN-VS was considered satisfactory when the targets were reached within 5%. After a given target level was reached and maintained for at least 500 beats, VVI pacing at a cycle length equal to the achieved target was added to the on-going AVN-VS and another 500 beats were collected. The order of the three levels of ventricular rate slowing was randomized. A recovery period of 5 minutes was allowed after each target study, although the AF was maintained uninterrupted.

AF produced irregular and rapid ventricular responses that resulted in an average ventricular rate substantially faster than the spontaneous sinus rate. The average R-R during AF was 287±36 ms, or 56% of the SCL (SCL=514±57 ms, n=8, P<0.01). AVN-VS successfully slowed average ventricular rate to each of the three target levels (achieved values=74%, 99%, and 123% of SCL, respectively).

Figure 4:
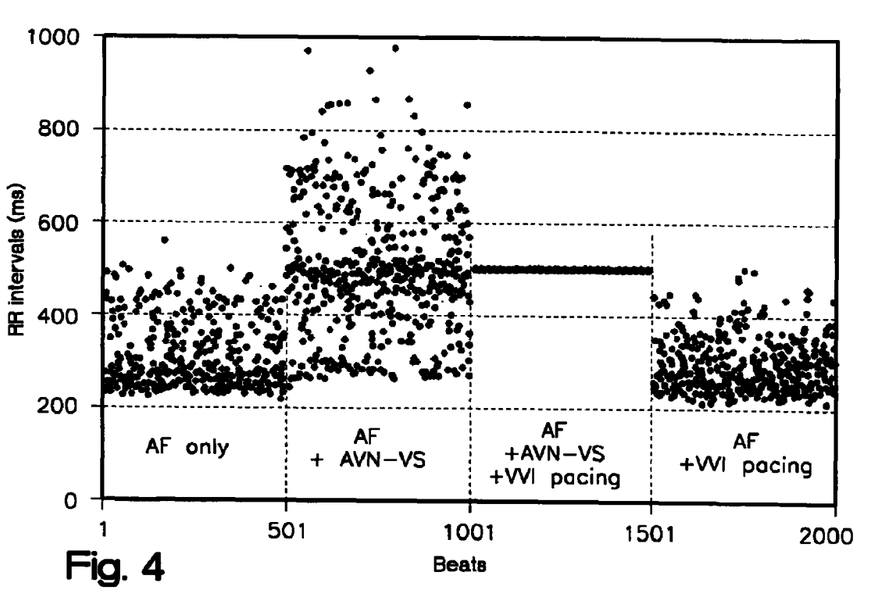
FIG. 4 is a chart illustrating the effectiveness of the present invention in normalizing R-R interval distributions in response to atrial fibrillation.

FIG. 4 shows an example of R-R interval distribution during AF (beats 1-500), with average R-R interval of 298 ms (corresponding to 201 bpm) and a standard deviation (SD) of 70 ms. AVN-VS prolonged the R-R intervals (i.e., ventricular rate was slowed). In this case, SCL was 510 ms (corresponding to 118 bpm), and the target was 100% SCL (beats 501-1000). The achieved average R-R interval was 505 ms but with a SD of 141 ms. Thus, compared with AF, AVN-VS reduced the average ventricular rate but not the irregularity.

When, in addition to AVN-VS, VVI pacing at a cycle length equal to the achieved target level (i.e., 505 ms) was initiated, it not only abolished all R-R intervals longer than the pacing interval but also eliminated all intervals shorter than the pacing interval (beats 1001-1500). Thus, a regular ventricular rhythm was immediately achieved and maintained. This regularity was just as immediately lost when AVN-VS was turned off (beats 1501-2000), indicating that AVN-VS was a crucially needed component of the complex pacing algorithm used to maintain regular ventricular rate.

Figure 5A:
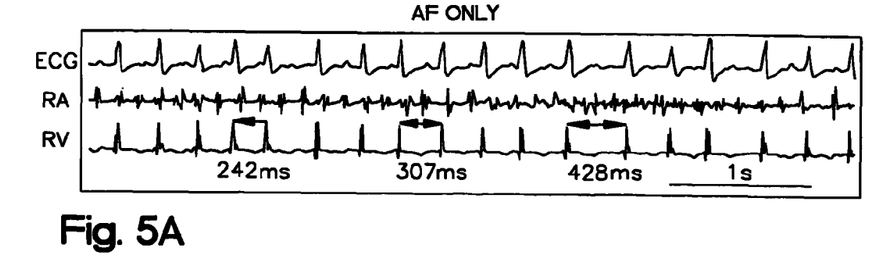
FIGS. 5A-5D are charts depicting ECG traces that illustrate the effectiveness of the present invention in treating atrial fibrillation.
Figure 5B:
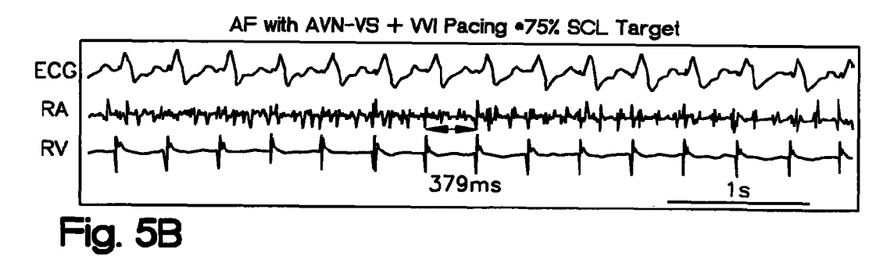
Figure 5C:
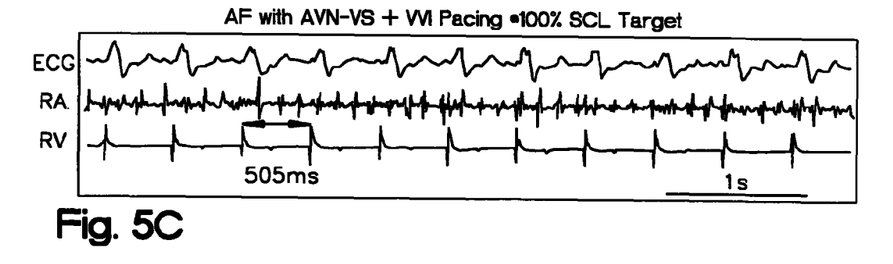
Figure 5D:
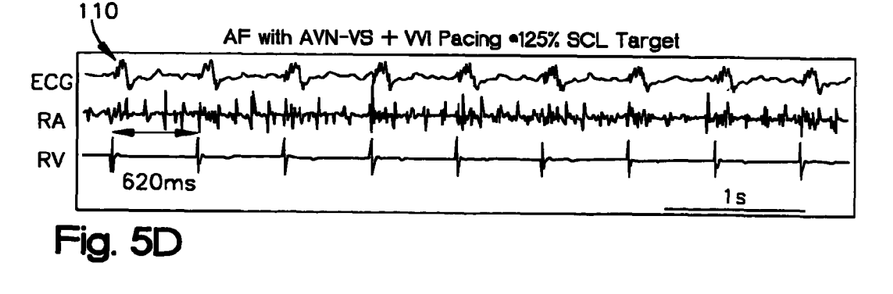
Figure 6A:
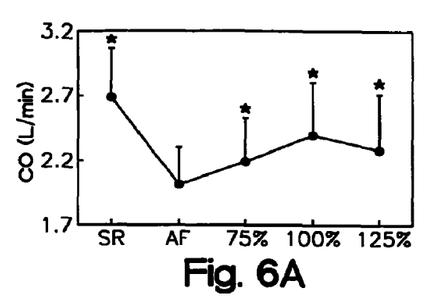
FIGS. 6A-6H are charts illustrating the improved hemodynamic performance realized by the present invention in response to atrial fibrillation.
Figure 6B:
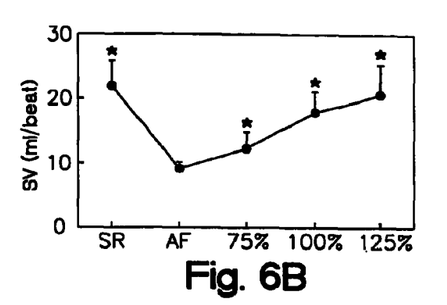
Figure 6C:
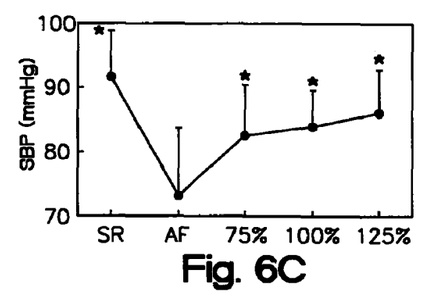
Figure 6D:
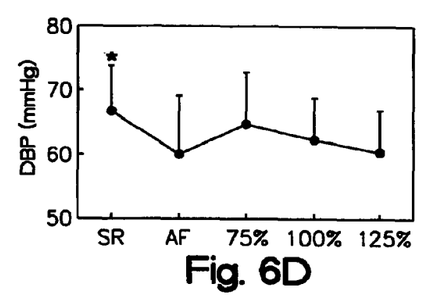
Figure 6E:
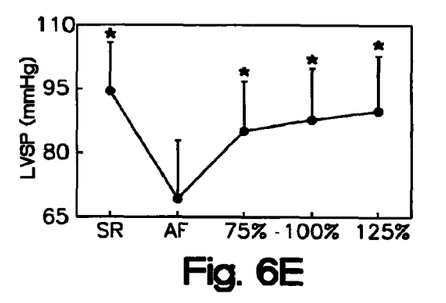
Figure 6F:
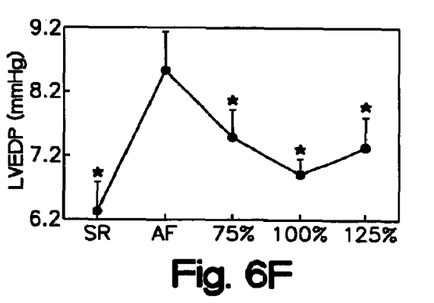
Figure 6G:
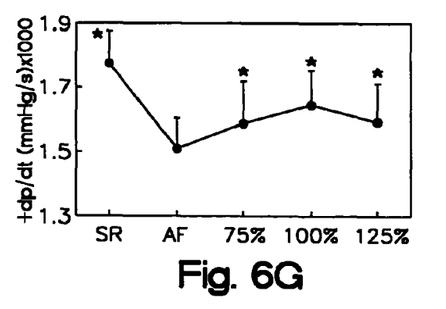
Figure 6H:
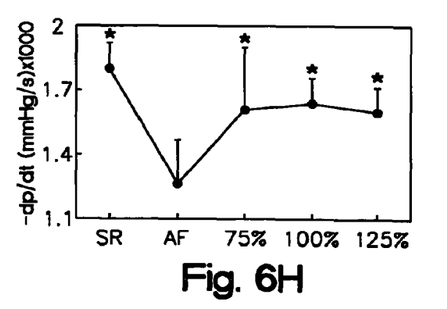

ECG traces from the same experiment are shown in FIGS. 5A-5D. FIG. 5A illustrates recordings during AF revealing the irregularity of the right ventricular electrograms (R-R range 242-428 ms in this episode). FIGS. 5B-5D illustrate episodes of combined delivery of AVN-VS and VVI pacing. In FIG. 5B, the AVN-VS intensity was first titrated to maintain the average ventricular rate during AF at a level corresponding to 75% SCL. The concomitant VVI pacing then resulted in constant R-R=379 ms (158 bpm). FIGS. 5C and 5D illustrate the outcome at 100% and 125% SCL, respectively. Again, progressively slower but strictly regular rhythms (R-R=505 ms [119 bpm] and 620 ms [97 bpm], respectively) were achieved in each case. The computer-controlled intensity of the brief AVN-VS bursts increased from 1.2 mA in FIG. 5B to 3.5 mA in FIG. 5D (where small artifacts produced by the brief AVN-VS bursts are indicated on the ECG at 110). Thus, by combining AVN-VS with VVI pacing, regular slow ventricular rhythms were achieved at each of the three target levels.

As set forth below, Table 1 lists the average R-R intervals and the corresponding standard deviation (SD) in each of the eight specimens (along with the composite data) during sinus rate, AF, after rate slowing by AVN-VS alone, and during AVN-VS plus VVI pacing. Note that although average ventricular rates were successfully controlled by AVN-VS alone (achieved average cycle lengths were within 2% of the corresponding targets), the rates still were very irregular, as evidenced by large SD. However, AVN-VS plus VVI pacing resulted not only in rate slowing but also in rhythm regularization (SD=0).

TABLE 1

| Specimen | SCL | AF | Target 75% SCL | | Target 100% SCL | | Target 125% SCL | |
|---|---|---|---|---|---|---|---|---|
| | | | AVN-VS | AVN-VS + VVI | AVN-VS | AVN-VS + VVI | AVN-VS | AVN-VS + VVI |
| 1 | 510 | 298 ± 70 | 379 ± 93 | 379 ± 0 | 505 ± 141 | 505 ± 0 | 620 ± 189 | 620 ± 0 |
| 2 | 540 | 257 ± 46 | 396 ± 89 | 396 ± 0 | 529 ± 121 | 529 ± 0 | 660 ± 133 | 660 ± 0 |
| 3 | 400 | 267 ± 22 | 298 ± 61 | 298 ± 0 | 398 ± 74 | 398 ± 0 | 497 ± 87 | 497 ± 0 |
| 4 | 480 | 271 ± 48 | 356 ± 59 | 356 ± 0 | 474 ± 77 | 474 ± 0 | 590 ± 105 | 590 ± 0 |
| 5 | 500 | 283 ± 21 | 373 ± 64 | 373 ± 0 | 498 ± 10 | 498 ± 0 | 625 ± 109 | 625 ± 0 |
| 6 | 580 | 304 ± 43 | 427 ± 98 | 427 ± 0 | 570 ± 13 | 570 ± 0 | 709 ± 129 | 709 ± 0 |
| 7 | 530 | 252 ± 37 | 397 ± 85 | 397 ± 0 | 529 ± 12 | 529 ± 0 | 658 ± 156 | 658 ± 0 |
| 8 | 570 | 365 ± 68 | 419 ± 82 | 419 ± 0 | 558 ± 14 | 558 ± 0 | 699 ± 167 | 699 ± 0 |
| Composite Mean | 514 ± 57 | 287 ± 36 | 381 ± 41 | 381 ± 41 | 508 ± 54 | 508 ± 54 | 632 ± 68 | 632 ± 68 |
| (% SCL) | (100%) | (56%) | (74%) | (74%) | (99%) | (99%) | (123%) | (123%) |

AF = atrial fibrillation;
SCL = sinus cycle length.

FIGS. 6A-6H illustrate the Improved hemodynamic responses realized through the application of the AVN-VS plus VVI pacing during AF in accordance with the present invention. In FIGS. 6A-6H, the hemodynamic parameters are shown as measured during sinus rhythm (SA), during atrial fibrillation (AF), and during AVN-VS plus VVI pacing at 75%, 100%, and 125% of the sinus cycle length (SCL). In FIGS. 6A-6H, plot points that include an asterisk (*) indicate values that are statistically significant over values experienced during AF (i.e., where P<0.05, as determined using post hoc Tukey's honestly significant difference test).

As shown in FIGS. 6A-6H, during AF, the measured hemodynamic parameters were significantly worsened compared to sinus rhythm. Regular slow rates achieved by AVN-VS plus VVI pacing during AF significantly improved all responses, with the exception that diastolic blood pressure (DSB, see FIG. 6D) improved only slightly and without statistical significance. In particular, systolic blood pressure (SBP, see FIG. 6C), LV systolic pressure (LVSP, see FIG. 6E), LV end-diastolic pressure (LVEDP, see FIG. 6F), ±dp/dt (see FIGS. 6G and 6H), stroke volume (SV, see FIG. 6B), and cardiac output (CO, see FIG. 6A) all improved significantly at each of the regular slow rates achieved by AVN-VS plus VVI pacing. Cardiac output, ±dp/dt, and LV end-diastolic pressure were best improved at a rate target corresponding to 100% SCL. This indicates that slowing the average ventricular rate to the level of the spontaneous sinus rhythm provided optimal overall hemodynamic benefits during AF.

The experimental data set forth above confirms that, with use of selective neural AVN-VS as a first step, subsequent regular VVI pacing at predetermined desired slow rates can be achieved. The slow, regular ventricular rates achieved by AVN-VS plus VVI pacing were associated with pronounced hemodynamic benefits that were rate dependent and permitted an optimal tune-up of the pacing protocol.

Based on the above, it will be appreciated that the system 10 of the present invention, capable of delivering VVI pacing along with AVN-VS, could achieve not only rate control but also regularization of the ventricular rhythm. The system 10 of the present invention could, for example, be embodied as a pace maker adapted to provide the on-demand pacing and AVN-VS functionality described above. The use of AVN-VS in combination with on-demand pacing may be preferable over ablation procedures and drug therapy, or may be used in addition to drug therapy.

Figure 7:
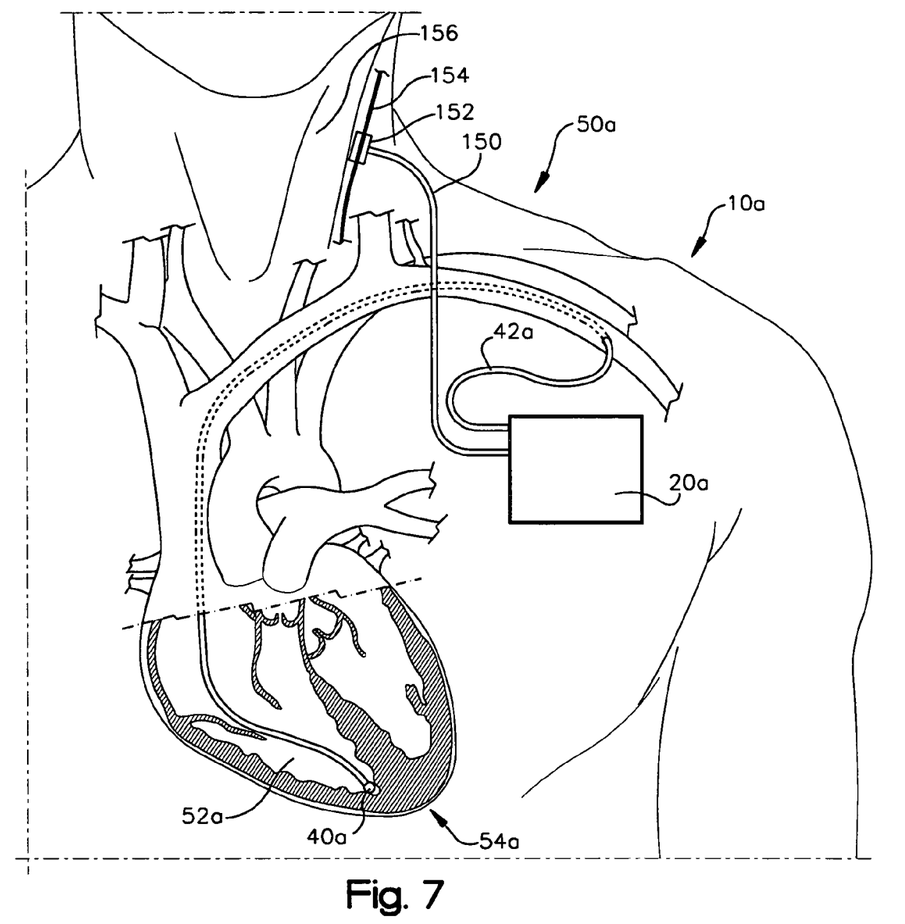
FIG. 7 is a schematic illustration of a system for treating cardiac arrhythmia in accordance with a second example embodiment of the present invention.

FIG. 7 illustrates an example configuration of a system 10a for combining AVN-VS with on-demand pacing to achieve a desired ventricular rate with a desired ventricular rhythm in response to AF. The system 10a of the second embodiment of the invention is similar to the system 10 of the first embodiment, except that the AVN-VS is administered in a manner that differs from that of the first embodiment. Therefore, in FIG. 7, reference numbers similar to those used to describe the first embodiment will be used to describe like elements, the suffix "a" being added to the reference numbers in FIG. 7 to avoid confusion.

The system 10a includes a control unit 20a, one or more vagal stimulation (VS) electrodes 152, and one or more pacing electrodes 40a. The VS electrodes 152 are operatively connected with the control unit 20a via VS leads 150. The pacing electrodes 40a are operatively connected with the control unit 20a via pacing leads 42a.

The control unit 20a is operative to provide electrical stimulation signals to the VS electrodes 152 and the pacing electrodes 40a via the leads 150 and 42a, respectively. The control unit 20a modulates or controls the frequency, amplitude, duration/pulse-width of the stimulation signals as described herein to achieve the desired ventricular rate and rhythm. The control unit 20a may also be operative to monitor cardiac activity, such as R waves, via the pacing electrodes 40a.

In FIG. 7, a patient 50a is outfitted with the system 10a of the second embodiment. The pacing electrodes 40a are delivered and implanted in the right ventricle 52a of the patient's heart 54a via blood vessels in a manner similar or identical to that described above in regard to the first embodiment. According to the second embodiment, VS electrodes 152 are implanted or otherwise positioned for stimulating left vagus nerves 154 of the patient 50a. In the embodiment of FIG. 7, the left vagus nerves 154 are cervical vagus nerves accessed through the patient's neck 156 via means, such as a catheterization or surgical procedure.

The control unit 20a may monitor electrical cardiac activity, such as R-R intervals, via the pacing electrodes 30a, in a manner similar or identical to that described above in regard to the first embodiment. This allows the system 10a to monitor the rate or rhythm of the heart 54a and detect the occurrence of atrial fibrillation. The system 10a thus may be an active or "on-demand" system in which ventricular rate and rhythm control is applied in response to detection to an AF episode.

In operation, the system 10a of the second embodiment operates in a manner similar or identical to that of the first embodiment as described above, with the exception that AVN-VS signals are delivered to the left cervical vagus nerve 154 as opposed to the AV nodal fat pad. The functional block diagram of FIG. 3 thus depicts a process performed by the system 10a of FIG. 7. More specifically, as shown in FIG. 3, the system 10a monitors electrical cardiac activity for the occurrence of atrial fibrillation. Upon detecting an AF episode, AVN-VS is applied to reduce the ventricular rate and ventricular (VVI) pacing is applied to help maintain a desired ventricular rhythm. Thus, according to the second embodiment of the present invention, the system 10a combines the AVN-VS and on-demand ventricular pacing to help achieve a regular slow ventricular rate in response to AF.

Figure 8:
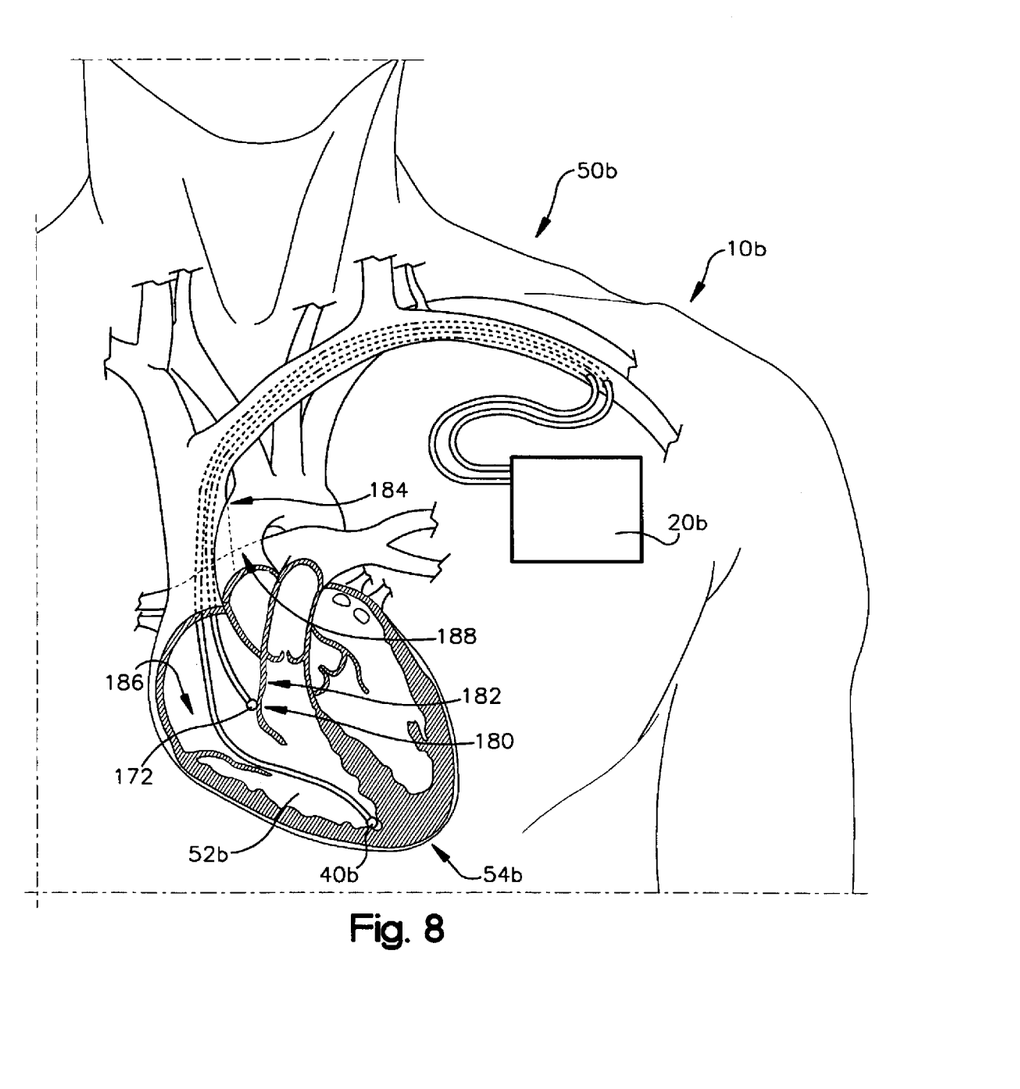
FIG. 8 is a schematic illustration of a system for treating cardiac arrhythmia in accordance with a third example embodiment of the present invention.

FIG. 8 illustrates an example configuration of a system 10b for combining AVN-VS with on-demand pacing to achieve a desired ventricular rate with a desired ventricular rhythm in response to AF. The system 10b of the third embodiment of the invention is similar to the systems 10 and 10a of the first and second embodiments, except that AVN-VS is administered in a manner that differs from those of the first and second embodiments. Therefore, in FIG. 8, reference numbers similar to those used to describe the first and second embodiments will be used to describe like elements, the suffix "b" being added to the reference numbers in FIG. 8 to avoid confusion.

The system 10b includes a control unit 20b, one or more vagal stimulation (VS) electrodes 172, and one or more pacing electrodes 40b. The VS electrodes 172 are operatively connected with the control unit 20b via VS leads 170. The pacing electrodes 40b are operatively connected with the control unit 20b via pacing leads 42b.

The control unit 20b is operative to provide electrical stimulation signals to the VS electrodes 172 and the pacing electrodes 40b via the leads 170 and 42b, respectively. The control unit 20b modulates or controls the frequency, amplitude, duration/pulse-width of the stimulation signals as described herein to achieve the desired ventricular rate and rhythm. The control unit 20b may also be operative to monitor cardiac activity, such as R waves, via the pacing electrodes 40b.

In FIG. 8, a patient 50b is outfitted with the system 10b of the third embodiment. The pacing electrodes 40b are delivered and implanted in the right ventricle 52b of the patient's heart 54b via blood vessels in a manner similar or identical to that described above in regard to the first embodiment.

According to the second embodiment, VS electrodes 172 are implanted or otherwise positioned for stimulating vagal nerve fibers indirectly via various endocardial structures. The embodiment of FIG. 8 illustrates various different alternative locations for endocardial placement of the VS electrodes 172. One location for endocardial placement of the VS electrodes 172 is the AV node 180. With this placement, the VS electrodes 172 apply post-ganglionic vagal stimulation to the AV node 180 directly. Another location for endocardial placement of the VS electrodes 172 is on the inside surface of the atrial wall as identified at 182 in FIG. 8. With this placement, the lead tip of the VS electrodes 172 will be in relatively close proximity to the AVN fat pad. Other locations for endocardial placement of the VS electrodes 172 include the interior wall of the superior vena cava 184, coronary sinus 186, or right pulmonary artery 188.

The control unit 20b may monitor electrical cardiac activity, such as R-R intervals, via the pacing electrodes 30b in a manner similar or identical to that described above in regard to the first embodiment. This allows the system 10b to monitor the rate or rhythm of the heart 54b and detect the occurrence of atrial fibrillation. The system 10b thus may be an active or "on-demand" system in which ventricular rate and rhythm control is applied in response to detection to an AF episode.

In operation, the system 10b of the third embodiment operates in a manner similar or identical to those of the first and second embodiments as described above, with the exception that AVN-VS signals are delivered to one or more of the endocardial locations set forth above, i.e., the AV node 180, atrial wall 182, superior vena cava 184, coronary sinus 186, or right pulmonary artery 188. The functional block diagram of FIG. 3 thus depicts a process performed by the system 10b of FIG. 8. More specifically, as shown in FIG. 3, the system 10b monitors electrical cardiac activity for the occurrence of atrial fibrillation. Upon detecting an AF episode, AVN-VS is applied to reduce the ventricular rate and ventricular (VVI) pacing is applied to help maintain a desired ventricular rhythm. Thus, according to the third embodiment of the present invention, the system 10b combines the AVN-VS and on-demand ventricular pacing to help achieve a regular slow ventricular rate in response to AF.

From the above description of the invention, those skilled in the art will perceive improvements, changes and modifications. Such improvements, changes and modifications within the skill of the art are intended to be covered by the appended claims.

Having described the invention, the following is claimed:

1. A system for achieving a desired cardiac rate and cardiac rhythm in response to atrial fibrillation in a heart, the system comprising:
    atrial fibrillation (AF) detecting means for detecting AF;
    atrioventricular node vagal stimulation (AVN-VS) means for applying electrical stimulation to an epicardial fat pad to stimulate vagal nerves associated with an atrioventricular (AV) node of the heart;
    on-demand pacing means for providing ventricular pacing stimulation to the heart; and
    control means operatively connected with the AF detecting means, the AVN-VS means, and the on-demand pacing means;
    the control means being responsive to AF detection by the AF detecting means to cause the AVN-VS means to stimulate the vagal nerves to help reduce a high irregular ventricular rate of the heart to a desired slower, though still irregular, ventricular rate of the heart;
    the control means being further responsive to AF detection by the AF detecting means to cause the on-demand pacing means to pace the heart at a regular rate equal to the average of the slower irregular ventricular rate achieved through vagal nerve stimulation in order to establish regular ventricular rhythm of the heart, wherein the AVN-VS means and the on-demand pacing means apply electrical stimulation simultaneously.

2. The system recited in claim 1, wherein the AVN-VS means comprises one or more AVN-VS electrodes, the control means being operative to provide stimulation signals to the AVN-VS electrodes in response to the detection of AF.

3. The system recited in claim 1, wherein the epicardial fat pad comprises an AV nodal fat pad of the heart.

4. The system recited in claim 1, wherein the AVN-VS means is operative to stimulate a vagus nerve to reduce the ventricular rate.

5. The system recited in claim 4, wherein the vagus nerve comprises a left vagus nerve.

6. The system recited in claim 1, wherein the on-demand pacing means comprises a VVI pacing electrode.

7. The system recited in claim 1, wherein the control means implements a closed loop control algorithm operative to adjust the intensity of energy applied by the AVN-VS means to help reduce the ventricular rate of the heart to the desired average rate.

8. The system recited in claim 1, wherein the control means implements a closed loop control algorithm operative to pace the heart via the on-demand pacing means at the rate equal to the average rate achieved through vagal nerve stimulation in order to maintain regularized ventricular rhythm.

9. A system for achieving a desired cardiac rate and cardiac rhythm in response to atrial fibrillation in a heart, the system comprising:
    an atrial fibrillation (AF) detector for detecting atrial fibrillation in the heart;
    an atrioventricular node vagal stimulation (AVN-VS) electrode for applying electrical stimulation to an epicardial fat pad to stimulate vagal nerves associated with an atrioventricular (AV) node of the heart;
    an on-demand pacing electrode for providing ventricular pacing stimulation to the heart; and
    a control unit operatively connected with the AF detector, the AVN-VS electrode, and the on-demand pacing electrode;
    the control unit being operative to determine an AF episode via the AF detector;
    the control unit being operative to provide an electrical signal to the AVN-VS electrode to stimulate the vagal nerves to help reduce a high irregular ventricular rate of the heart to a desired slower, though still irregular rate in response to determining an AF episode;
    the control unit, in response to determining an AF episode, being further operative to provide an electrical signal to the on-demand pacing electrode to pace the heart at a regular rate equal to the average of the slower irregular ventricular rate achieved through vagal nerve stimulation in order to establish regular ventricular rhythm of the heart, wherein the AVN-VS electrode and the on-demand pacing electrode apply electrical stimulation simultaneously.

10. The system recited in claim 9, wherein the AF detector comprises at least a portion of the on-demand pacing electrode.

11. The system recited in claim 9, wherein the control unit implements a closed loop control algorithm operative to pace the heart via the pacing electrodes at the rate equal to the average rate achieved through vagal nerve stimulation in order to maintain regularized ventricular rhythm.

12. A method for achieving a desired cardiac rate and cardiac rhythm in response to atrial fibrillation in a heart, the method comprising the steps of:
    applying electrical stimulation to an epicardial fat pad to stimulate vagal nerves associated with an atrioventricular (AV) node of the heart to reduce high irregular cardiac rate to a desired slower average rate; and
    applying ventricular pacing stimulation at a rate equal to the average slower rate achieved through vagal nerve stimulation in order to help establish regular ventricular rhythm of the heart, wherein the step of applying ventricular pacing is performed once the cardiac rate is reduced by stimulating the vagal nerves and continues thereafter simultaneously with the application of electrical stimulation to the vagal nerves.

13. The method recited in claim 12, wherein the step of applying electrical stimulation to an epicardial fat pad to stimulate vagal nerves comprises the step of applying electrical stimulation to the vagal nerves via an atrioventricular node vagal stimulation (AVN-VS) electrode.

14. The method recited in claim 12, wherein the step of applying electrical stimulation to an epicardial fat pad to stimulate vagal nerves comprises the step of stimulating an AV nodal fat pad to reduce the ventricular rate.

15. The method recited in claim 12, wherein the step of applying electrical stimulation to an epicardial fat pad to stimulate vagal nerves comprises the step of stimulating a vagus nerve to reduce the ventricular rate.

16. The method recited in claim 15, wherein the step of stimulating a vagus nerve comprises the step of stimulating a left vagus nerve.

17. The method recited in claim 12, wherein the step of applying electrical stimulation to an epicardial fat pad comprises applying electrical stimulation to an epicardial fat pad to reduce the cardiac rate to the desired cardiac rate and the step of applying ventricular pacing stimulation comprises applying ventricular pacing stimulation at the desired cardiac rate.

18. The system recited in claim 12, wherein the step of applying ventricular pacing stimulation comprises implementing a closed loop control algorithm operative to pace the heart at the rate equal to the average rate achieved through vagal nerve stimulation in order to maintain regularized ventricular rhythm.

19. A method for achieving a desired cardiac rate and cardiac rhythm in response to atrial fibrillation in a heart, the method comprising the steps of:
  applying electrical stimulation to an epicardial fat pad to stimulate vagal nerves associated with an atrioventricular (AV) node of the heart to reduce high irregular cardiac rate to a desired slower average rate; and
  applying ventricular owing stimulation at a rate equal to the average slower rate achieved through vagal nerve stimulation in order to help establish regular ventricular rhythm of the heart, wherein the step of applying electrical stimulation to an epicardial fat pad and the step of applying ventricular pacing stimulation are performed simultaneously.

* * * * *

UNITED STATES PATENT AND TRADEMARK OFFICE
CERTIFICATE OF CORRECTION

PATENT NO.        : 7,860,566 B2                              Page 1 of 1
APPLICATION NO.   : 11/244896
DATED             : December 28, 2010
INVENTOR(S)       : Todor N. Mazgalev et al.

It is certified that error appears in the above-identified patent and that said Letters Patent is hereby corrected as shown below:

Column 14, line 12, after "applying ventricular" delete "owing" and insert --pacing--

Signed and Sealed this

Fifteenth Day of February, 2011

David J. Kappos
*Director of the United States Patent and Trademark Office*